US010675253B2

(12) United States Patent
Kevil et al.

(10) Patent No.: US 10,675,253 B2
(45) Date of Patent: Jun. 9, 2020

(54) METHODS OF DIAGNOSIS AND TREATMENT INVOLVING NITRITE

(71) Applicant: Board of Supervisors of Louisiana State University and Agricultural and Mechanical College, Baton Rouge, LA (US)

(72) Inventors: Christopher Kevil, Shreveport, LA (US); Sibile Pardue, Shreveport, LA (US)

(73) Assignee: BOARD OF SUPERVISORS OF LOUISIANA STATE UNIVERSITY, Baton Rouge, LA (US)

(*) Notice: Subject to any disclaimer, the term of this patent is extended or adjusted under 35 U.S.C. 154(b) by 0 days.

(21) Appl. No.: 15/935,581

(22) Filed: Mar. 26, 2018

(65) Prior Publication Data

US 2018/0271802 A1 Sep. 27, 2018

Related U.S. Application Data

(60) Provisional application No. 62/477,715, filed on Mar. 28, 2017, provisional application No. 62/477,176, (Continued)

(51) Int. Cl.
*A61K 31/105* (2006.01)
*A61K 38/44* (2006.01)
(Continued)

(52) U.S. Cl.
CPC ............ *A61K 31/105* (2013.01); *A61K 33/00* (2013.01); *A61K 38/44* (2013.01); *A61P 9/10* (2018.01);
(Continued)

(58) Field of Classification Search
CPC ...... A61K 31/105; A61K 38/44; A61K 33/00; C12Y 117/03002; G01N 33/84; G01N 2800/32; A61P 9/10
See application file for complete search history.

(56) References Cited

U.S. PATENT DOCUMENTS 9,599,602 B2* 3/2017 Kevil ................. G01N 33/84
2013/0209584 A1* 8/2013 Kevil ................. A61K 9/2068
424/718

* cited by examiner

*Primary Examiner* — Trevor Love
(74) *Attorney, Agent, or Firm* — Davis & Bujold PLLC; Charles Holoubek

(57) ABSTRACT

Methods and therapeutics for treating nitric oxide (NO) mediated condition comprising administering a therapeutically effective amount of a pharmaceutical composition containing a therapeutic, wherein the therapeutic one of increases xanthine oxidase (XO) associated nitrite conversion to nitric oxide and increases nitrite conversion to nitric oxide via DADS. Method and devices for measuring an amount of nitrite in a sample comprising obtaining a sample, adding diallyl disulfide (DADS) to the sample, measuring a post DADS amount of nitric oxide (NO) in the sample, and using the post DADS amount of NO in the sample to determine the amount of nitrite in the sample. Methods and therapeutics for diagnosing and treating critical limb ischemia (CLI) versus non-critical limb ischemic peripheral artery disease (PAD) in a patient comprising determining a patient indicator value, where the patient indicator is value one of a total hydrogen sulfide metabolite plasma level, a total nitric oxide, nitrite, and nitrite (NOx) plasma level, a ratio of free hydrogen sulfide plasma level to total NOx plasma level, and a ratio of total hydrogen sulfide metabolite plasma level and total NOx plasma level, diagnosing the patient with as having CLI based on the patient indicator value, and administering to the patient a therapeutic for CLI.

17 Claims, 12 Drawing Sheets

Related U.S. Application Data filed on Mar. 27, 2017, provisional application No. 62/477,090, filed on Mar. 27, 2017, provisional application No. 62/476,526, filed on Mar. 24, 2017, provisional application No. 62/476,501, filed on Mar. 24, 2017, provisional application No. 62/476,487, filed on Mar. 24, 2017, provisional application No. 62/476,552, filed on Mar. 24, 2017.

(51) Int. Cl.
    *G01N 33/84*     (2006.01)
    *A61P 9/10*     (2006.01)
    *A61K 33/00*     (2006.01)

(52) U.S. Cl.
    CPC ...... *C12Y 117/03002* (2013.01); *G01N 33/84* (2013.01); *G01N 2800/32* (2013.01)

Ascorbic Acid

DADs

DATs

METHODS OF DIAGNOSIS AND TREATMENT INVOLVING NITRITE

CROSS REFERENCE TO RELATED APPLICATIONS/PRIORITY

The present invention claims priority to U.S. Provisional Patent Application No. 62/477,090 filed Mar. 27, 2017, U.S. Provisional Patent Application No. 62/477,176 filed Mar. 27, 2017, U.S. Provisional Patent Application No. 62/477,715 filed Mar. 28, 2017, U.S. Provisional Patent Application No. 62/476,487 filed Mar. 24, 2017, U.S. Provisional Patent Application No. 62/476,501 filed Mar. 24, 2017, U.S. Provisional Patent Application No. 62/476,552 filed Mar. 24, 2017, and U.S. Provisional Patent Application No. 62/476,526 filed Mar. 24, 2017, which are all incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

STATEMENT REGARDING FEDERALLY SPONSORED RESEARCH OR DEVELOPMENT

This invention was made with government support under Grant No. HL113303 awarded by the National Institutes of Health. The government has certain rights in the invention.

BACKGROUND

While it has been shown that increasing NO levels can be therapeutic for a number of conditions, the biochemical mechanism of nitrite reduction to NO, and thereby increasing NO levels, is poorly understood. Nitrite reduction in vivo occurs through different pathways, however efficiency of nitrite reduction in vivo is difficult to control or augment. Some agents can facilitate such reduction, such as ascorbic acid, but do so weakly. Strong biocompatible agents to stimulate nitrite reduction to NO are not available in current technology.

Nitrite levels in an organism are important to know, but nitrite is difficult to measure in solution.

While proper diagnosis is an important factor in timely appropriate treatment of underlying disease, non-critical limb ischemic peripheral artery disease (PAD) and critical limb ischemia (CLI) can be difficult to distinguish and accurately diagnose, beyond the limited clinical diagnosis of ankle brachial index or claudication.

SUMMARY

Wherefore, various embodiments of the disclosed invention are directed at overcoming respective above mentioned shortcomings and drawbacks associated with the current technology.

On embodiment of the disclosed invention is directed to therapeutics and method of treating nitric oxide (NO) mediated condition comprising administering a therapeutically effective amount of a pharmaceutical composition containing a therapeutic wherein the therapeutic one of increases xanthine oxidase (XO) associated nitrite conversion to nitric oxide and increases nitrite conversion to nitric oxide via DADS. According to an additional embodiment, the therapeutic increases XO and the therapeutic includes diallyl trisulfide (DATS) or a pharmacologically acceptable salt, solvate, ester, amide, clathrate, stereoisomer, enantiomer, prodrug or analog thereof, or combination thereof. According to an additional embodiment, the therapeutic further includes one of XO, nitrite, both XO and nitrite, and pharmacologically acceptable salts, solvates, esters, amides, clathrates, stereoisomers, enantiomers, prodrugs or analogs thereof, or combinations thereof. According to an additional embodiment, the therapeutic increases nitrite conversion to nitric oxide via DADS and therapeutic includes DADS or a pharmacologically acceptable salt, solvate, ester, amide, clathrate, stereoisomer, enantiomer, prodrug or analog thereof, or combination thereof. According to an additional embodiment, the therapeutic further includes one of nitrite and a pharmacologically acceptable salt, solvate, ester, amide, clathrate, stereoisomer, enantiomer, prodrug or analog thereof, or combination thereof. According to an additional embodiment, the NO mediated condition includes one of inflammation, wound healing, and an infection.

A further embodiment of the disclosed invention is directed to devices and methods of measuring an amount of nitrite in a sample comprising obtaining a sample, adding diallyl disulfide (DADS) to the sample, measuring a post DADS amount of nitric oxide (NO) in the sample, and using the post DADS amount of NO in the sample to determine the amount of nitrite in the sample. According to an additional embodiment, a pre DADS amount of NO in the sample is measured before the DADS is added to the sample and subtracting the pre DADS amount of NO in the sample from the post DADS amount of NO in the sample in determining the amount of nitrite in the sample.

A yet further embodiment of disclosed invention is directed to devices, therapeutics, and methods of diagnosing and treating critical limb ischemia (CLI) versus peripheral artery disease which is not critical limb ischemic (PAD) in a patient comprising determining a patient indicator value, where the patient indicator value is one of a total hydrogen sulfide metabolite plasma level, a total nitric oxide, nitrite, and nitrite (NOx) plasma level, a ratio of free hydrogen sulfide plasma level to total NOx plasma level, and a ratio of total hydrogen sulfide metabolite plasma level and total NOx plasma level, diagnosing the patient with as having CLI based on the patient indicator value, and administering to the patient a therapeutic for CLI. According to an additional embodiment, the patient is diagnosed with CLI when the indicator value is total hydrogen sulfide plasma level and the total hydrogen sulfide plasma level is one of less than 0.75 µM, less than 0.70 µM, less than 0.65 µM, less than 0.60 µM, and less than 0.55 µM. According to an additional embodiment, the patient is diagnosed with CLI when the indicator value is total hydrogen sulfide plasma level and the total hydrogen sulfide plasma level is less than 80% of an average total hydrogen sulfide plasma level for PAD patients. According to an additional embodiment, the patient is diagnosed with CLI when the indicator value is total NOx plasma level and the total NOx plasma level is one of over 220 nM, over 200 nM, over 175 nM, and over 150 nM. According to an additional embodiment, the patient is diagnosed with CLI when the indicator value is total NOx plasma level and the total NOx plasma level is one of more two times, more than three times, and more than fourth times of an average total NOx plasma level for PAD patients. According to an additional embodiment, the patient is diagnosed with CLI when the indicator value is the ratio of free hydrogen sulfide plasma level to total NOx plasma level and the ratio of free hydrogen sulfide plasma level to total NOx plasma level is one of less than 5.0, or less than 3.0, and less than 2.0. According to an additional embodiment, the patient is diagnosed with CLI when the indicator value is the ratio of free hydrogen sulfide plasma level to total NOx plasma level and the ratio of free hydrogen sulfide plasma level to total NOx plasma level is one of less than one half, less than one third, less than one fourth, less than one fifth, and less than one sixth of an average ratio of free hydrogen sulfide plasma level to total NOx plasma level for PAD patients. According to an additional embodiment, the patient is diagnosed with CLI when the indicator value is the ratio of total hydrogen sulfide metabolite plasma level and total NOx plasma level and the ratio of total hydrogen sulfide metabolite plasma level and total NOx plasma level is one of less than 10 and less than 5. According to an additional embodiment, the patient is diagnosed with CLI when the indicator value is the ratio of total hydrogen sulfide metabolite plasma level and total NOx plasma level and the ratio of total hydrogen sulfide metabolite plasma level and total NOx plasma level is one of less than one half, less than one third, less than one fourth, and less than one fifth of an average ratio of total hydrogen sulfide metabolite plasma level and total NOx plasma level for PAD patients.

The present invention relates to therapeutics and methods of treatment of various conditions by increasing XO associated nitrite conversion to nitric oxide.

The present invention further relates to methods and kits to measure nitrite levels in various assay forms.

The present invention further relates to therapeutics and methods of treatment of various conditions by increasing nitrite conversion to nitric oxide via DADS.

The present invention further relates to devices and methods of diagnosing CLI versus PAD via total hydrogen sulfide levels, including subsequent treatment.

The present invention further relates to devices and methods of diagnosing CLI versus PAD via total nitrite levels, including subsequent treatment.

The present invention further relates to devices and methods of diagnosing CLI versus PAD via FHS to TNO levels, including subsequent treatment.

The present invention further relates to devices and methods of diagnosing CLI versus PAD via THS to TNO levels, including subsequent treatment.

The present invention relates to pharmaceutical compositions of a therapeutic (e.g., DADS, DATS, XO, nitrite, L-propionyl-carnitine, Prostaglandin E1, and aspirin), or a pharmaceutically acceptable salt, solvate, ester, amide, clathrate, stereoisomer, enantiomer, prodrug or analogs thereof, and use of these compositions for the treatment of a NO mediated condition, including inflammation, wound healing, critical limb ischemia, peripheral artery disease, and an infection In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is a NO mediated condition.

In certain embodiments, the NO mediated condition is mild to moderate NO mediated condition.

In further embodiments, the NO mediated condition is moderate to severe NO mediated condition.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the NO mediated condition.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coaterie), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% A of the agent is released within the first 30 minutes, 45 minutes, or 60 minutes of administration.

The term "pharmaceutical composition," as used herein, includes a composition containing a compound described herein (e.g., DADS, DATS, XO, nitrite, L-propionyl-carnitine, Prostaglandin E1, and aspirin, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., a NO mediated condition). Treatment can be initiated, for example, prior to ("pre-exposure prophylaxis")

or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Pharmaceutical Compositions

The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $22^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, $8^{th}$ Edition, Sheskey et al., Eds., Pharmaceutical Press (2017), which is incorporated by reference.

The methods described herein can include the administration of a therapeutic, or prodrugs or pharmaceutical compositions thereof, or other therapeutic agents. Exemplary therapeutics include those that increase nitrite conversion to NO (including DADS) and those that selectively increases XO dependent nitrite reduction to NO (including DATS).

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1.3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art (see, e.g., Biesalski, U.S. Pat. No. 5,112,598, and Biesalski, U.S. Pat. No. 5,556,611).

Formulations for sublingual administration can also be used, including powders and aerosol formulations. Exemplary formulations include rapidly disintegrating tablets and liquid-filled soft gelatin capsules.

Dosing Regimes

The present methods for treating NO mediated conditions are carried out by administering a therapeutic for a time and in an amount sufficient to result in decreased symptoms of the condition, such as deceased pain or increased wound healing, for example.

The amount and frequency of administration of the compositions can vary depending on, for example, what is being administered, the state of the patient, and the manner of administration. In therapeutic applications, compositions can be administered to a patient suffering from NO mediated conditions in an amount sufficient to relieve or least partially relieve the symptoms of the NO mediated conditions and its complications. The dosage is likely to depend on such variables as the type and extent of progression of the NO mediated conditions, the severity of the NO mediated conditions, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the NO mediated conditions or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-25 µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the NO mediated conditions.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION

Figure 1:
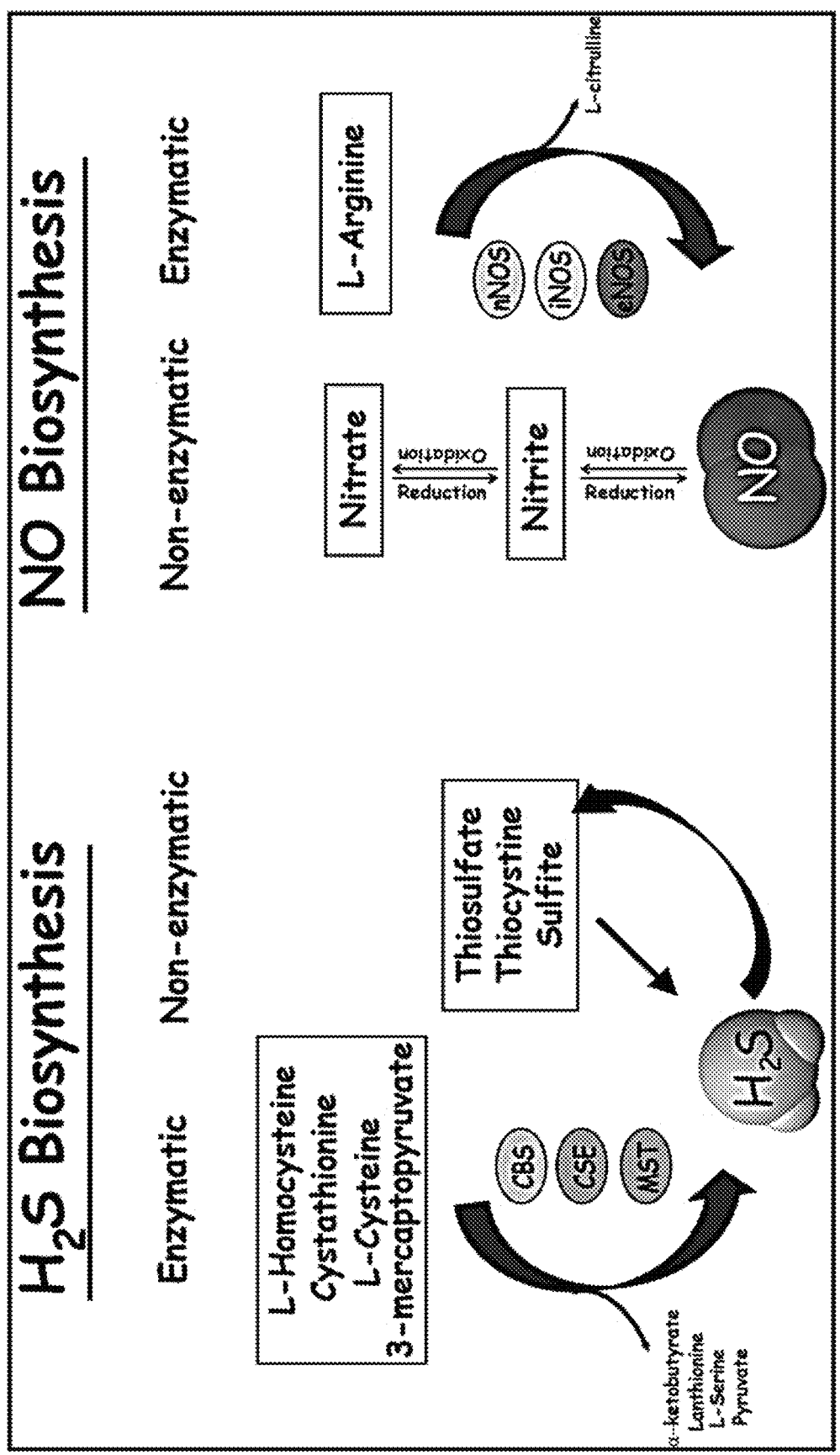
FIG. 1 is a schematic representation of enzymatic and non-enzymatic gasotransmitter biosynthesis.
Figure 2:
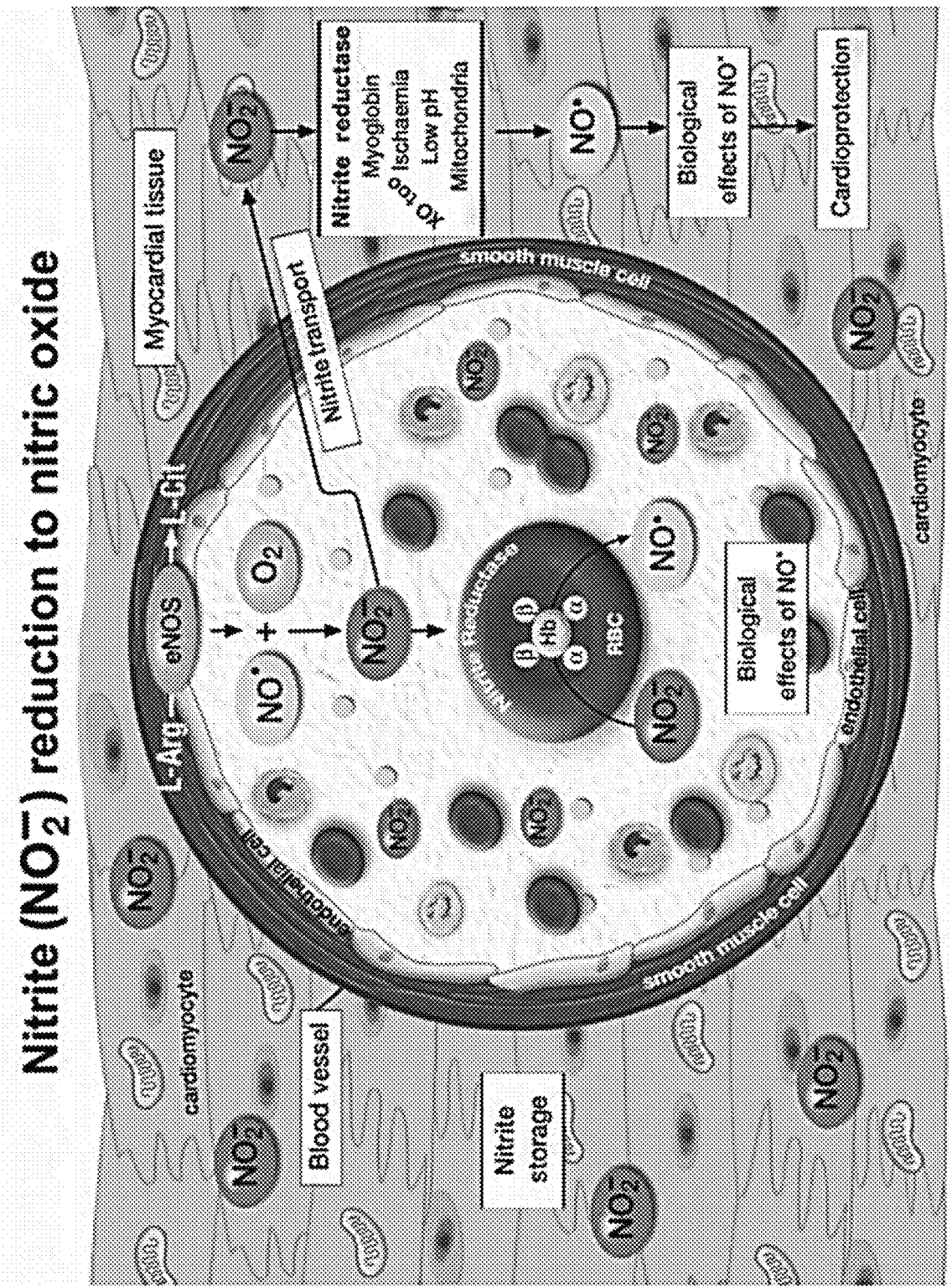
FIG. 2 is a schematic representation of an overview of nitrite reduction to NO.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

With reference to FIGS. 1-12, a brief description concerning the various components of various embodiments of the disclosed invention will now be briefly discussed.

Figure 3:
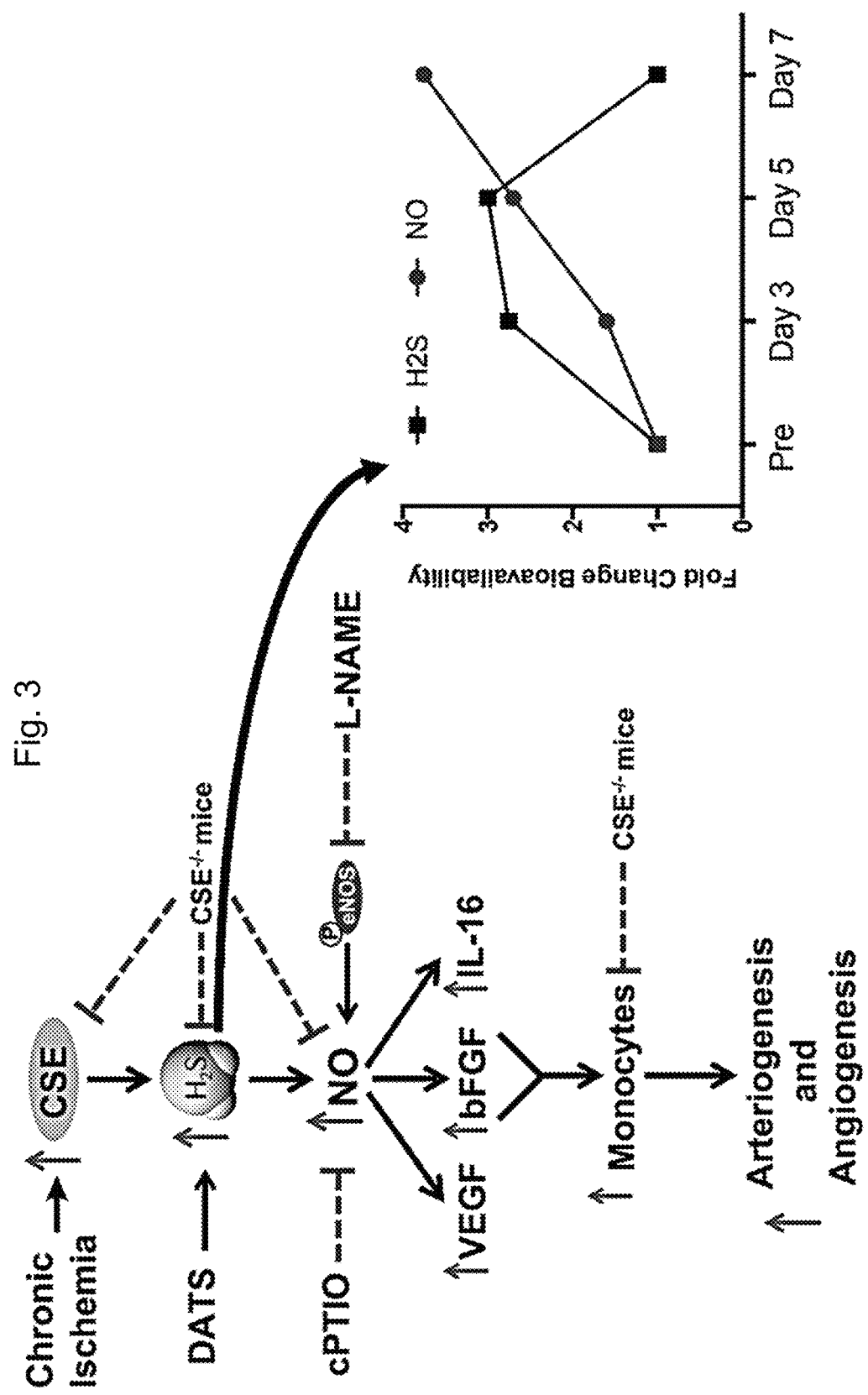
FIG. 3 is a schematic representation and line graph of H2S and NO regulation of ischemic vascular remodeling.
Figure 4:
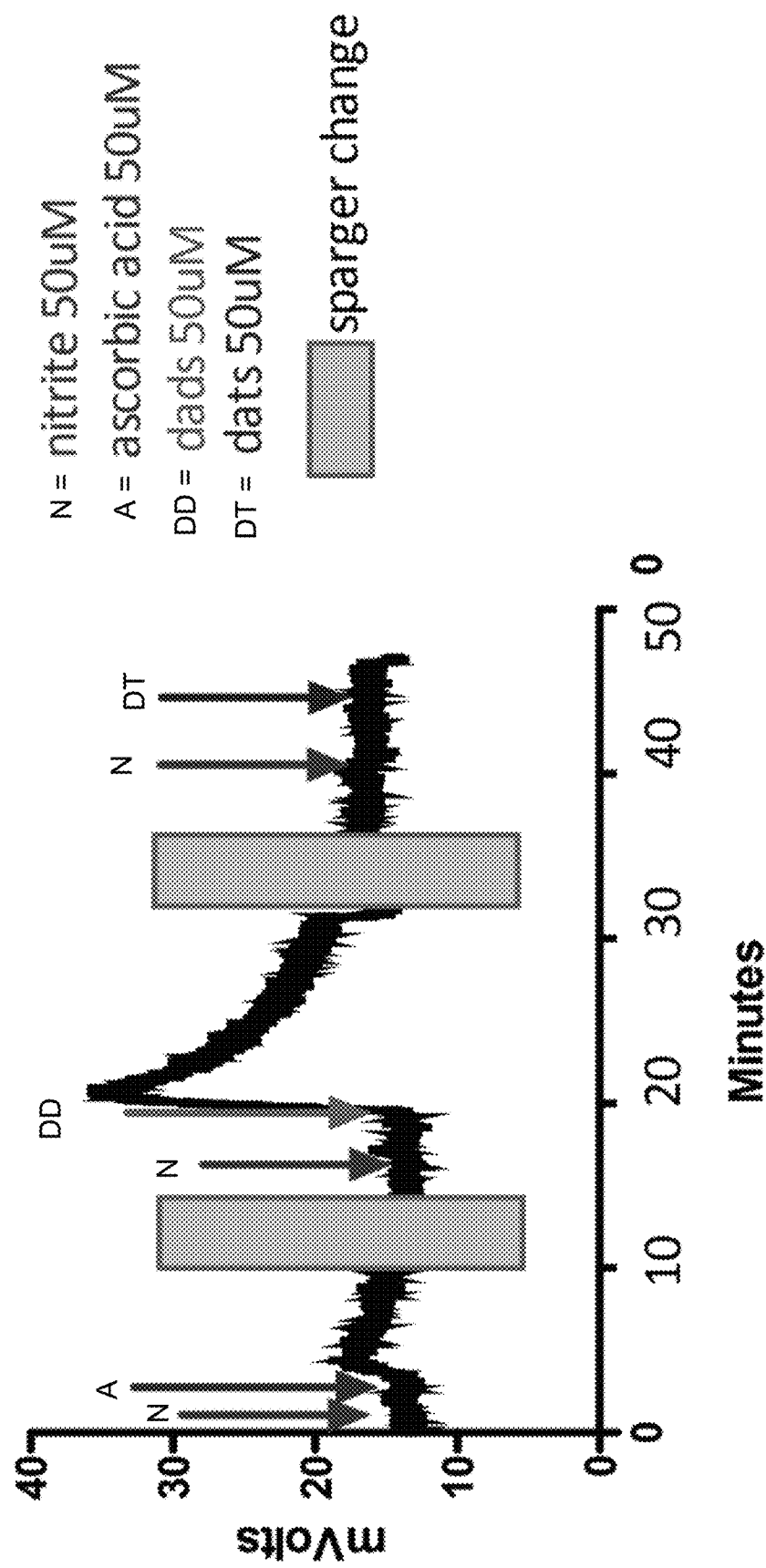
FIG. 4 is a line graph of experiments showing nitrite reduction to NO facilitated by ascorbic acid, DADS, or DATS.
Figure 5:
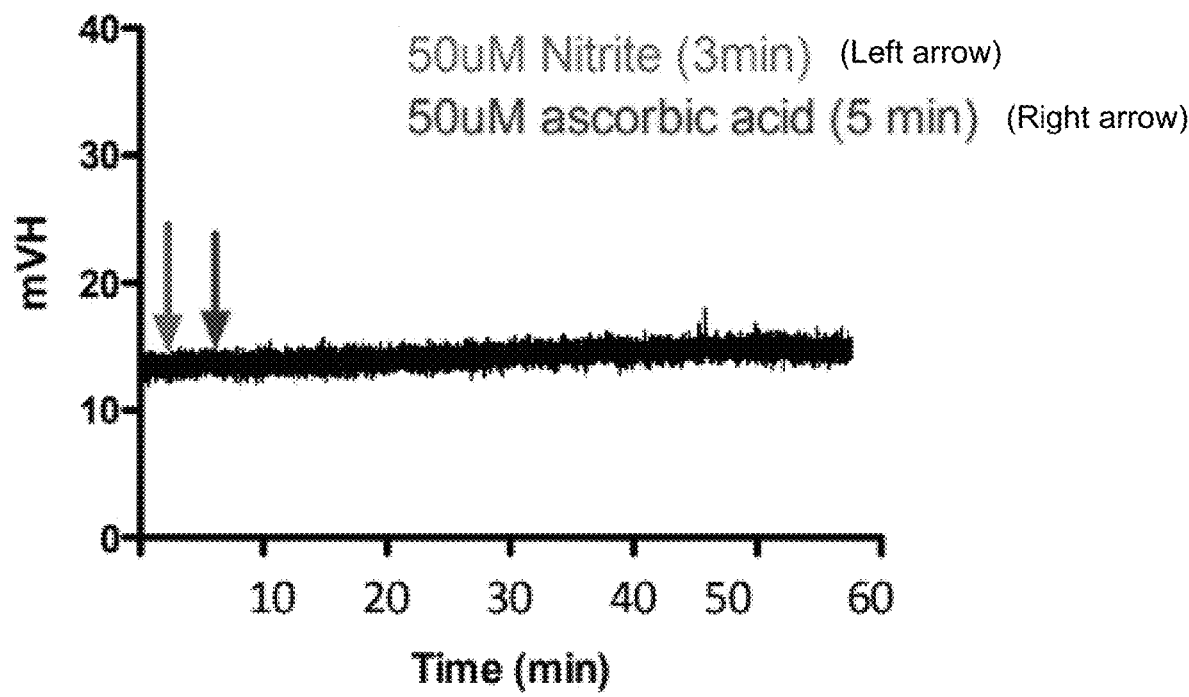
FIG. 5 is a pair of line graphs of two experiments showing nitrite reduction to NO facilitated by ascorbic acid over one hour.
Figure 5:
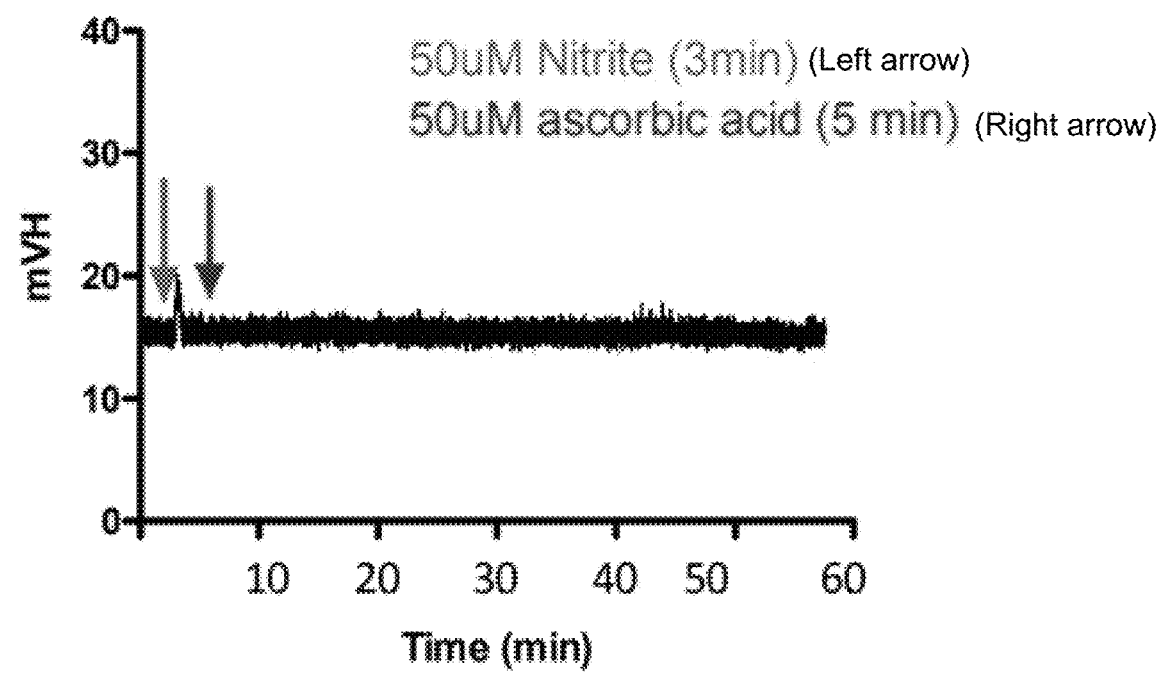
Figure 6:
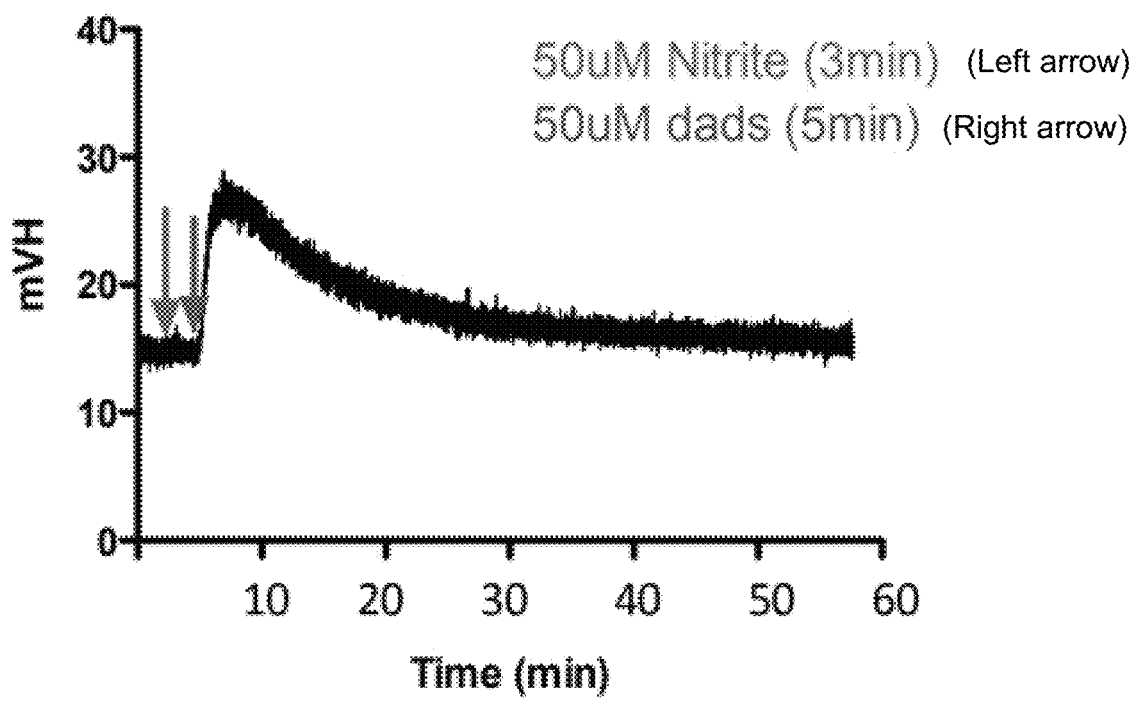
FIG. 6 is a pair of line graphs of two experiments showing nitrite reduction to NO facilitated by DADS over one hour.
Figure 6:
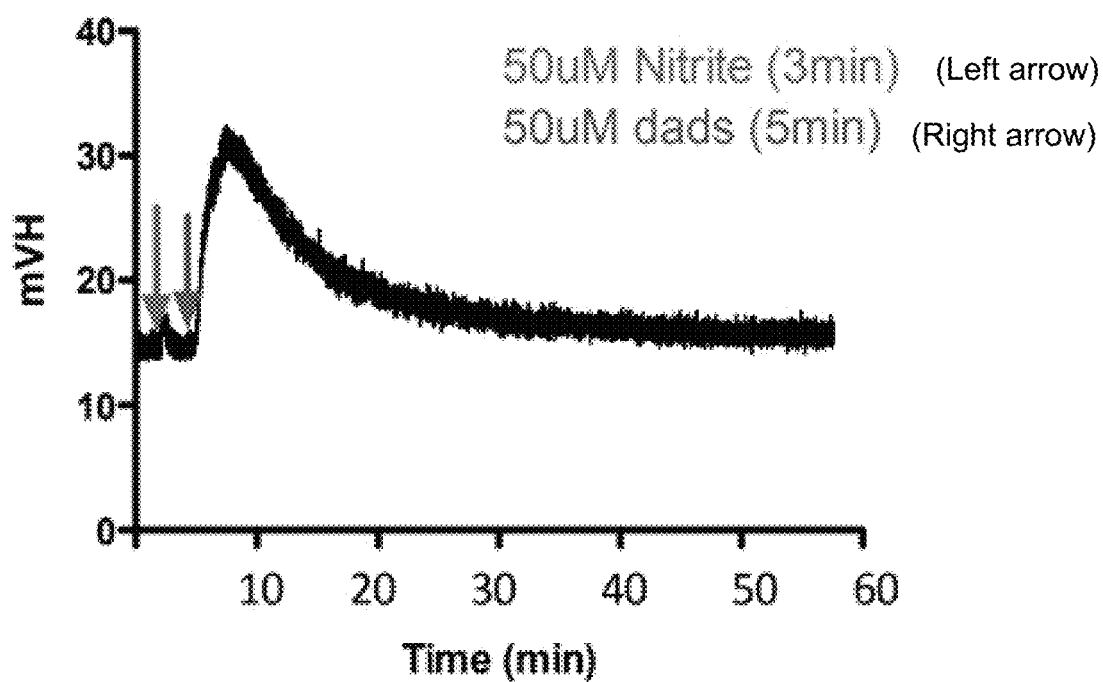
Figure 7:
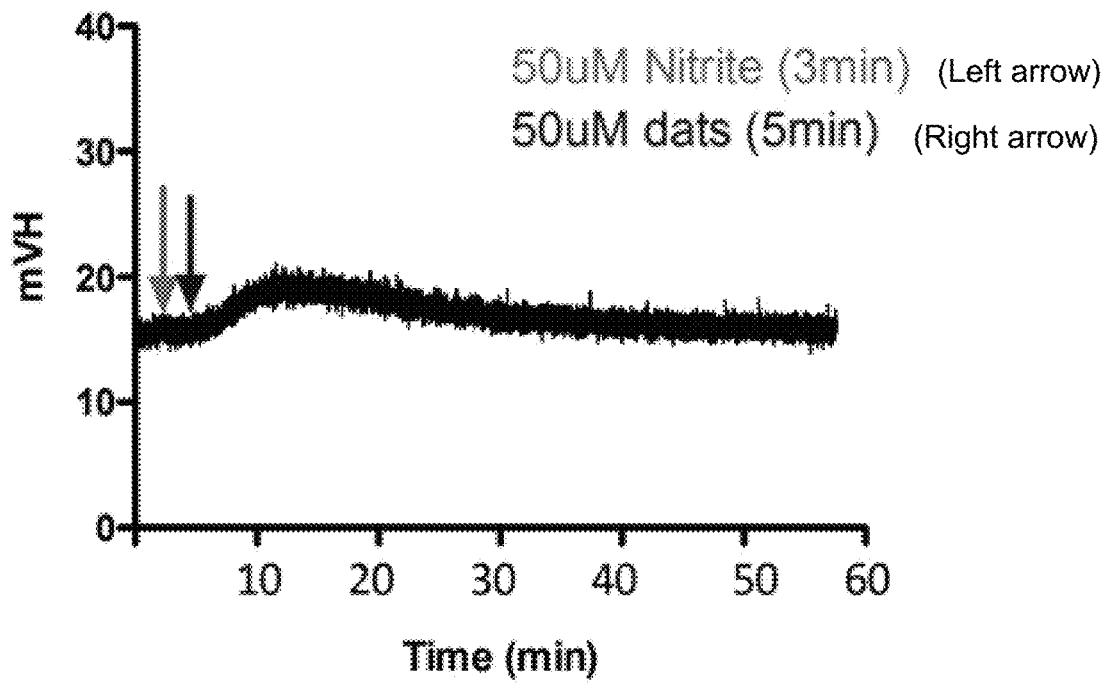
FIG. 7 is a pair of line graphs of two experiments showing nitrite reduction to NO facilitated by DATS over one hour.
Figure 7:
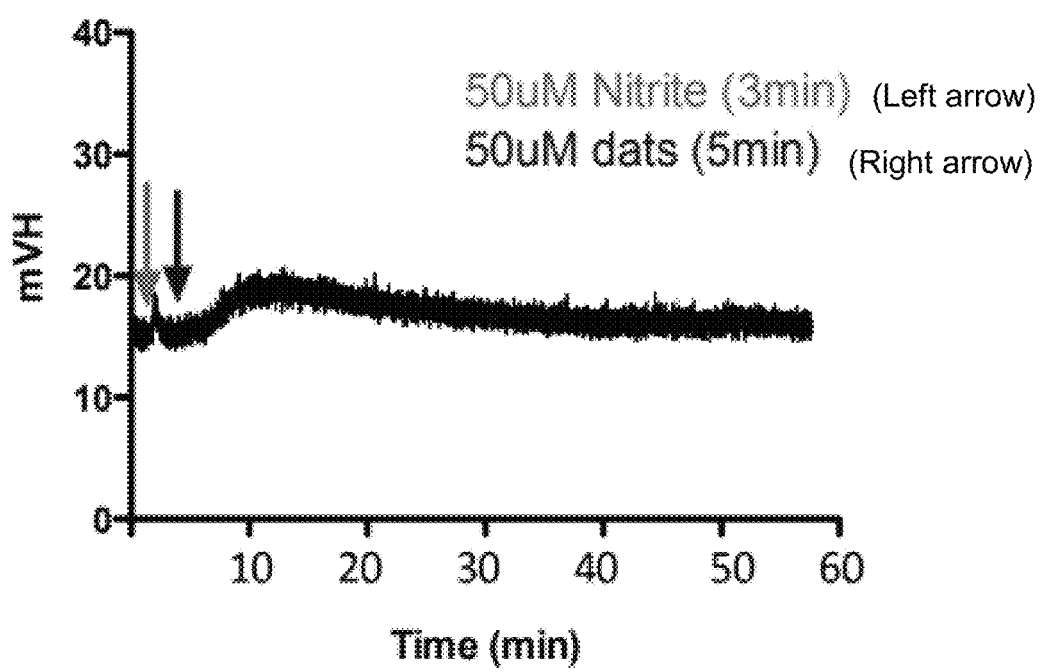
Figure 8:
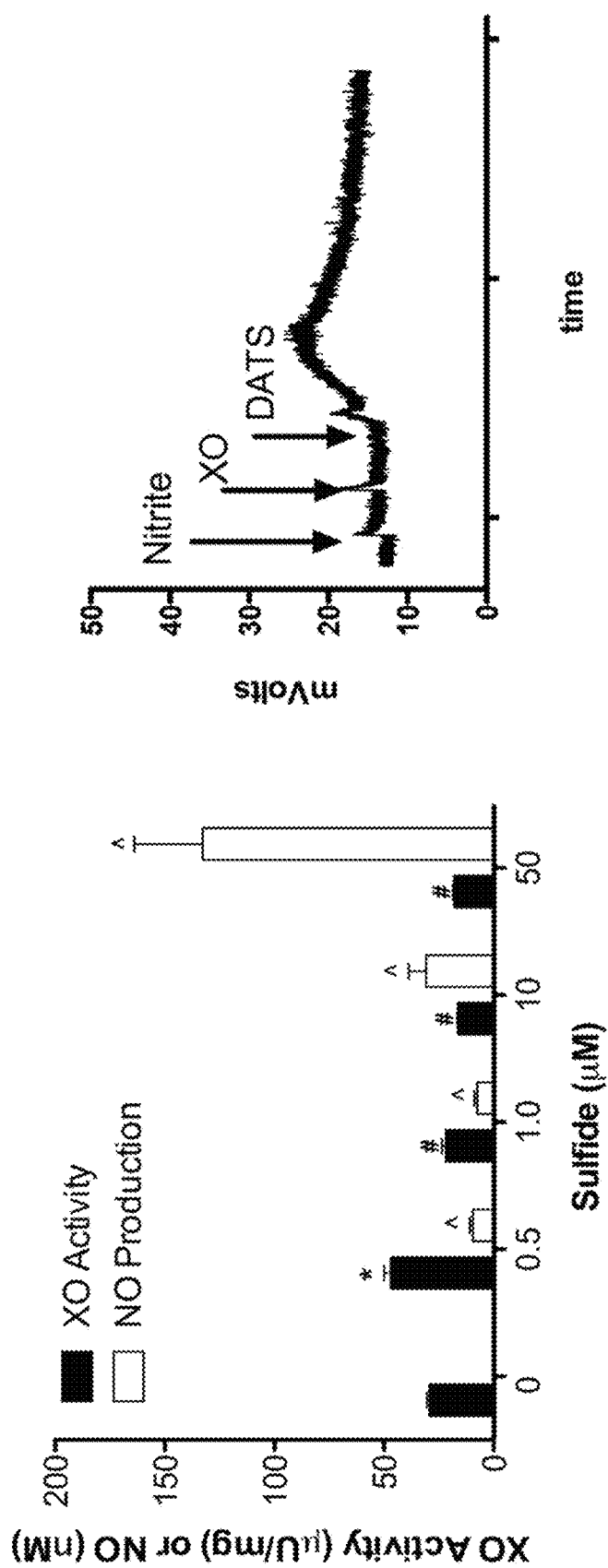
FIG. 8 is a bar chart and a line graph showing DATS differentially affects XO activity & NO production.
Figure 9:
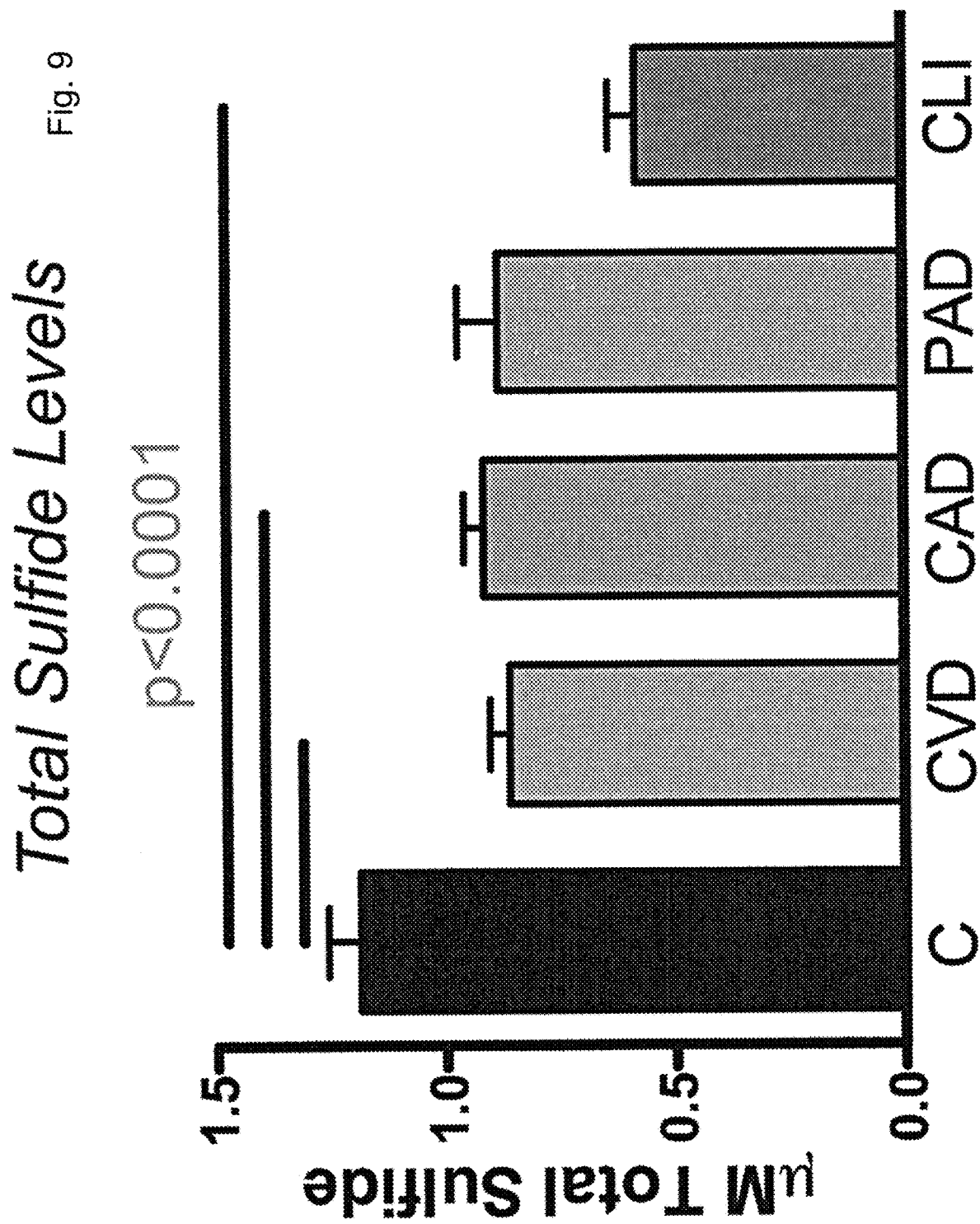
FIG. 9 is a bar chart showing total sulfide plasma levels for control and patients suffering from CVD, CAD, PAD, and CLI.
Figure 10:
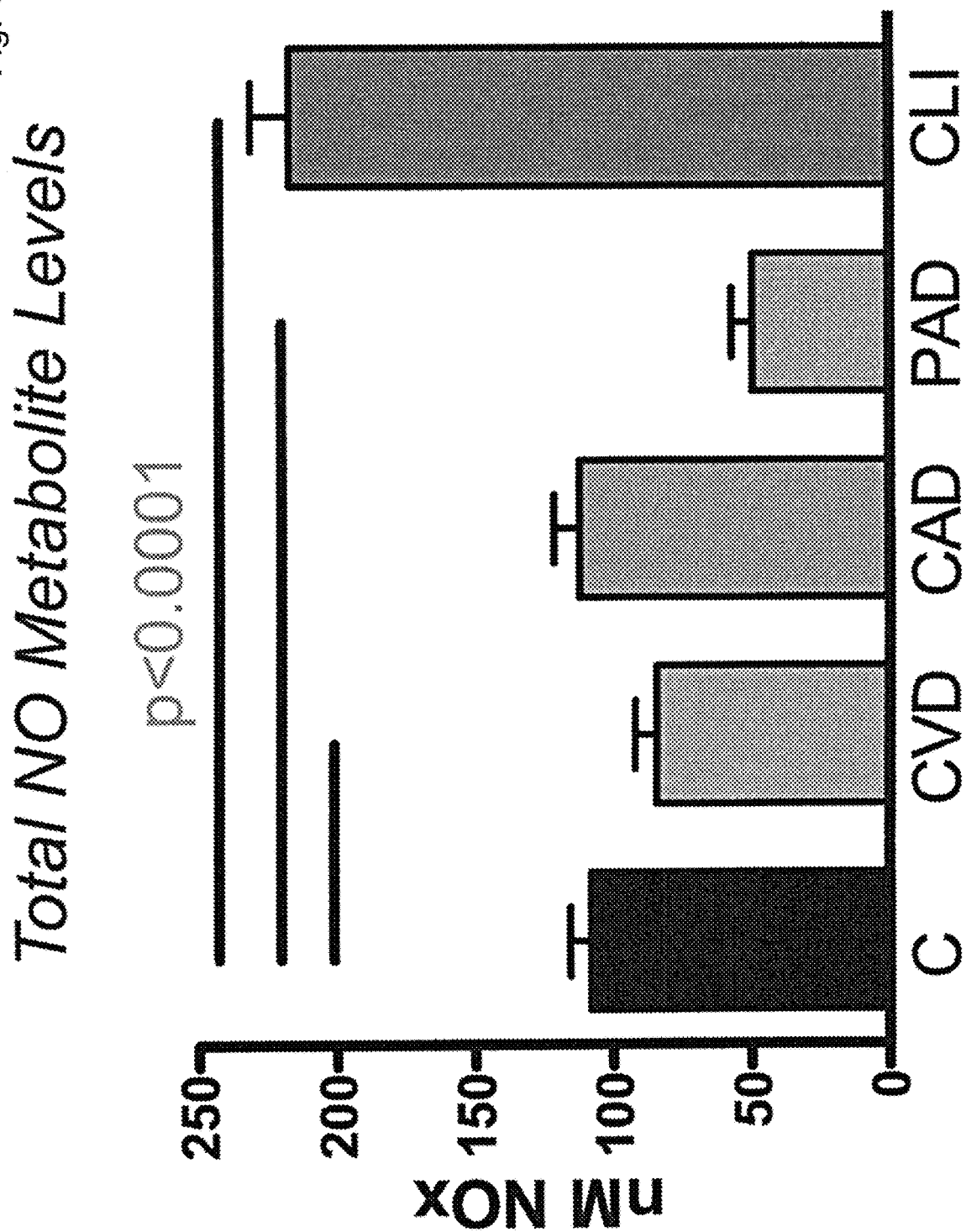
FIG. 10 is a bar chart showing total NO metabolite plasma levels for control and patients suffering from CVD, CAD, PAD, and CLI.

Nitric oxide is one of the most potent cardiovascular health regulating molecules known Nitrite is a prodrug for NO formation that is beneficial for vascular function and growth Turning to FIGS. 1-7, an embodiment of the disclosed invention, including a method of treatment of various conditions by increasing nitrite conversion to nitric oxide via DADS is described. This embodiment of the disclosed invention describes chemical reactions that may be useful for stimulating nitrite conversion to nitric oxide, namely diallyl disulfide (DADS) reduction of nitrite to nitric oxide. As shown in FIG. 3, the inventors' findings show Sulfide levels rapidly increase that subsequently augments NO bioavailability. This would be useful for various purposes including unique ways to stimulate nitrite reduction to nitric oxide within an organism.

While it has been shown that increasing NO levels can be therapeutic for a number of conditions, the biochemical mechanism of nitrite reduction to NO, and thereby increasing NO levels, is poorly understood. Some agents can facilitate such reduction, such as ascorbic acid, but do so weakly. Strong biocompatible agents to stimulate nitrite reduction to NO are not available in current technology. DADS was discovered by the inventors to selectively stimulate nitrite reduction to NO. DADS may therefore be administered as a therapeutic for known NO mediated conditions, including inflammation, wound healing, and infections. DADS, and pharmacologically acceptable salt, solvate, ester, amide, clathrate, stereoisomer, enantiomer, prodrug or analog thereof, or combination thereof can be administered in a variety of methods, including nanoformulation compounds, especially for creams or lotions. One embodiment of the invention is a method of treating a NO mediated condition by administering to a mammal, preferably human, a therapeutically effective amount of diallyl disulfide or a pharmacologically acceptable salt, solvate, ester, amide, clathrate, stereoisomer, enantiomer, prodrug or analog thereof, or combination thereof. The DADS may be administered alone, or, for example, with nitrite This is the first biocompatible agent known to the inventors to selectively and strongly stimulate nitrite reduction to NO; also derived from natural product.

The embodiments could include therapeutics including medications and nutraceuticals.

Referring to FIGS. 1-8, a further embodiment of the disclosed invention, including a method of treatment of various conditions by increasing XO associated nitrite conversion to nitric oxide is described. This embodiment of the disclosed invention describes chemical reactions that may be useful for stimulating xanthine oxidase (XO) to increase nitrite conversion to nitric oxide, namely diallyl trisulfide (DATS) stimulation of XO reduction of nitrite to nitric oxide. This would be useful for various purposes including unique ways to stimulate nitrite reduction to nitric oxide within an organism.

While it has been shown that increasing NO levels can be therapeutic for a number of conditions, the biochemical mechanism of nitrite reduction to NO, and thereby increasing NO levels, is poorly understood. Nitrite reduction in vivo occurs through different pathways, however efficiency of nitrite reduction in vivo is difficult to control or augment. Some agents can facilitate such reduction, such as ascorbic acid, but do so weakly. Strong biocompatible agents to stimulate nitrite reduction to NO are not available in current technology.

The inventors discovered that DATS selectively increases XO dependent nitrite reduction to NO. DATS may therefore be administered alone, or for example, with nitrite and/or XO, as a therapeutic for known NO mediated conditions, including inflammation, wound healing, and infections. DATS can be administered in a variety of methods, including nanoformulation compounds, especially for creams or lotions.

One embodiment of the invention is a method of treating a NO mediated condition by administering to a mammal, preferably human, a therapeutically effective amount of diallyl trisulfide or a pharmacologically acceptable salt, solvate, ester, amide, clathrate, stereoisomer, enantiomer, prodrug or analog thereof, or a combination thereof. The DATS may be administered alone, or, for example, with nitrite, XO, or both.

This is the first biocompatible agent known to the inventors to selectively and strongly stimulate XO dependent nitrite reduction to NO; also derived from natural product.

The embodiments could include therapeutics including medications and nutraceuticals.

Based on experimental evidence, combined nitrite and DATS formulation would augment XO dependent nitrite reduction to NO, yielding many cardio vascular therapy uses Next, a method and kit to measure nitrite levels in various assay forms is described. Nitrite is difficult to measure in solution, while nitric oxide is much more readily measurable. Based on the discovery of diallyl disulfide (DADS) reduction of nitrite to nitric oxide, the invention allows for a new indirect method to measure the amount of nitrite in a solution. The nitrite containing solution is reacted with DADS, producing nitric oxide, and the nitric oxide is then measured. The nitric oxide level may also be measured before the nitrite solution is reacted with DADS to account for any nitric oxide that may already be present in the solution. This would be useful for various purposes including unique ways to measure nitrite bioavailability in an assay and to measure progress of treatment or disease.

It is anticipated that one embodiment of this invention will be integrated in a kit for measurement, preferably with DADS included in the kit. It is anticipated that a further embodiment will incorporate the measuring into a machine and/or a lab on a chip and/or computer device.

Figure 12:
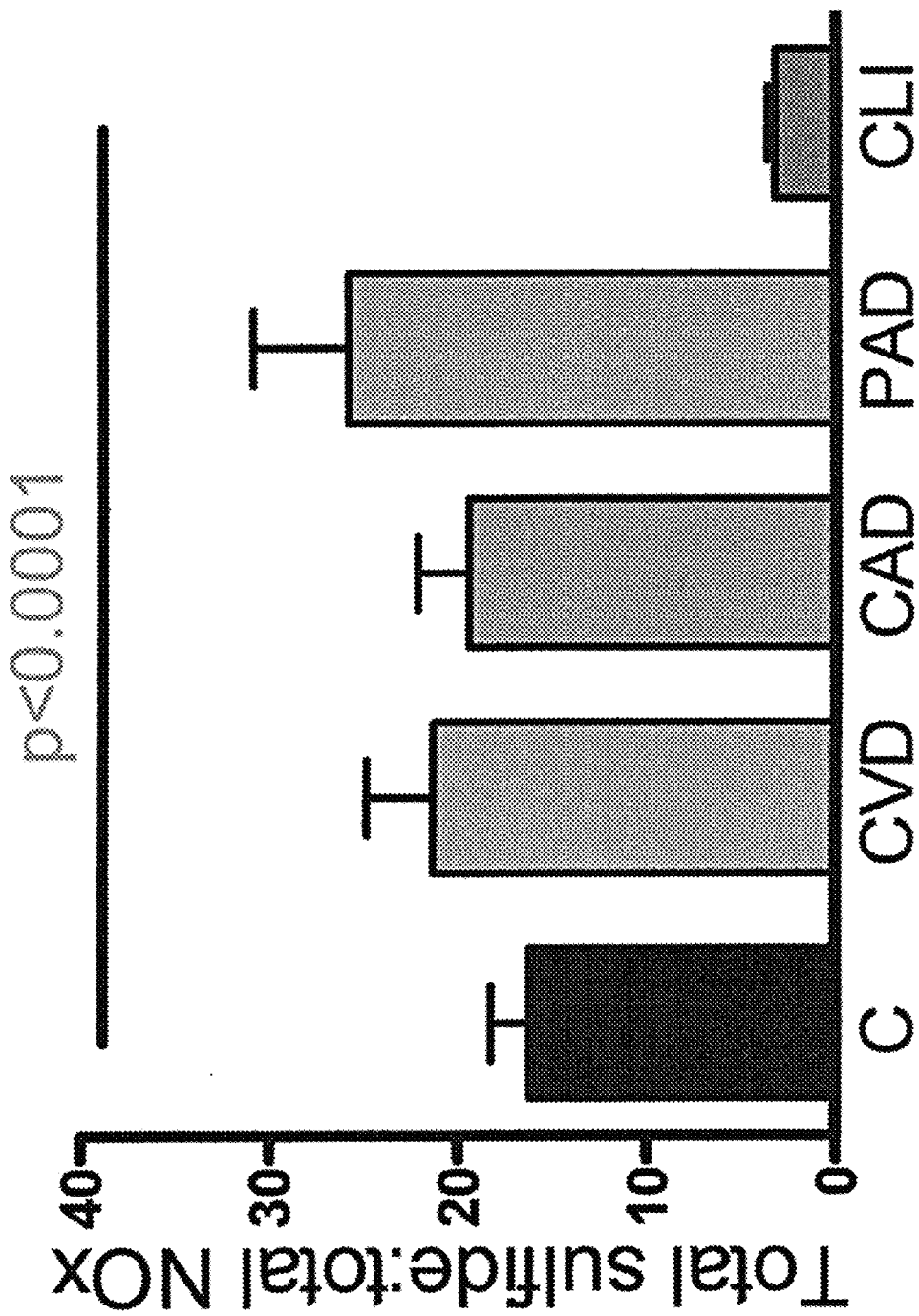
FIG. 12 is a bar chart showing the ratio of total sulfide to total NO metabolite plasma levels for control and patients suffering from CVD, CAD, PAD, and CLI.

Turning to FIG. 12, a further embodiment of the disclosed invention, including a method of diagnosing CLI versus PAD via total hydrogen sulfide levels is described. This embodiment of the disclosed invention employs measurement of plasma sulfide metabolites to clinically determine peripheral artery disease versus critical limb ischemia. Specifically, the level of total hydrogen sulfide delineates between peripheral artery disease versus critical limb ischemia. The total hydrogen sulfide level was found to be lower in CLI patients than PAD patients. In one embodiment, CLI is diagnosed when the total hydrogen sulfide level is less than 0.75 µM, less than 0.70 µM, less than 0.65 µM, less than 0.60 µM, or less than 0.55 µM. In another embodiment CLI is diagnosed when the total hydrogen sulfide level is less than 80% of a total hydrogen sulfide level for PAD patients. This method may also provide a useful therapeutic indicator for clinical interventions that may be followed over time. This method can be used in a diagnostic kit. The embodiment may include treating for CLI or PAD respectively with currently known treatments once the appropriate diagnosis is made.

One product of this embodiment of the disclosed invention would be a method to detect peripheral artery disease or critical limb ischemia beyond the limited clinical diagnosis of ankle brachial index or claudication. A secondary product would be a treatment target to clinically treat disease. Treatment with L-propionyl-carnitine and/or Prostaglandin E1, aspirin, and therapeutics which increase NO levels, including sodium nitrite and therapeutics that increase xanthine oxidase (XO) associated nitrite conversion to nitric oxide and/or increase nitrite conversion to nitric oxide via DADS, for example, may follow diagnosis of CLI.

The technology could be used to accurately diagnose PAD or CLI that is currently imprecise in clinical settings. The approach would also be useful as a point of care device to confirm sulfide and/or nitric oxide levels.

Turning to FIG. 12, a further embodiment of the disclosed invention, including a method of diagnosing CLI versus PAD via total nitrite levels is described. This embodiment of the disclosed invention employs measurement of plasma sulfide metabolites to clinically determine peripheral artery disease versus critical limb ischemia. Specifically, the level of total nitrite delineates between peripheral artery disease versus critical limb ischemia. The total nitrite level was found to be higher in CLI patients than PAD patients. In one embodiment, CLI is diagnosed when the total nitrite level is over 220 nM, over 200 nM, over 175 nM, or over 150 nM. In another embodiment CLI is diagnosed when the total nitrite level is more 2 times, more than three times, more than fourth times of a total nitrite level for PAD patients. This method may also provide a useful therapeutic indicator for clinical interventions that may be followed over time. This method can be used in a diagnostic kit. The embodiment may include treating for CLI or PAD respectively with currently known treatments once the appropriate diagnosis is made.

One product of this embodiment of the disclosed invention would be a method to detect peripheral artery disease or critical limb ischemia beyond the limited clinical diagnosis of ankle brachial index or claudication. A secondary product would be a treatment target to clinically treat disease. Treatment with L-propionyl-carnitine and/or Prostaglandin E1, aspirin, and therapeutics which increase NO levels, including sodium nitrite and therapeutics that increase xanthine oxidase (XO) associated nitrite conversion to nitric oxide and/or increase nitrite conversion to nitric oxide via DADS, for example, may follow diagnosis of CLI.

The technology could be used to accurately diagnose PAD or CLI that is currently imprecise in clinical settings. The approach would also be useful as a point of care device to confirm sulfide and/or nitric oxide levels.

Figure 11:
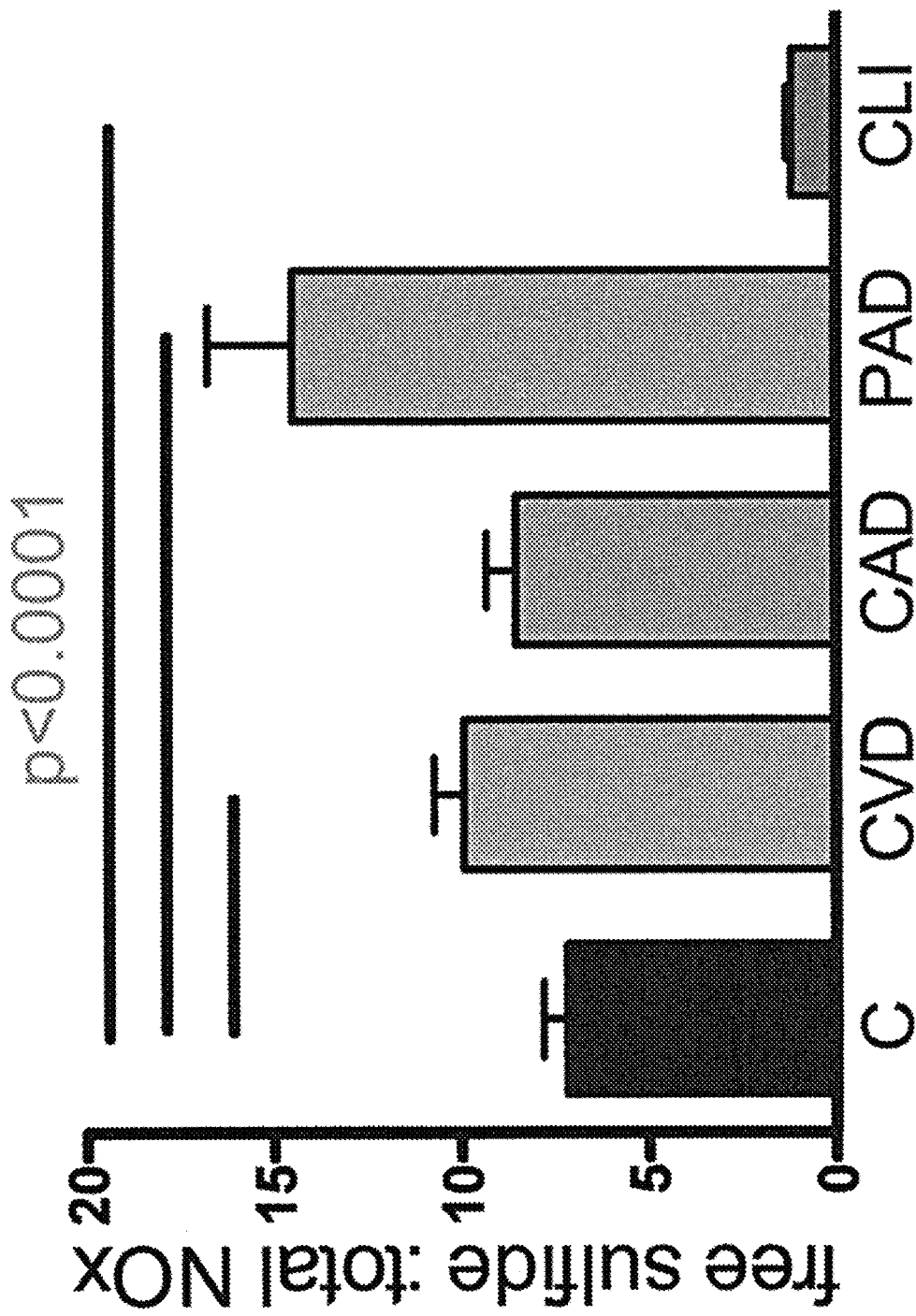
FIG. 11 is a bar chart showing the ratio of free H2S to total NO metabolite plasma levels for control and patients suffering from CVD, CAD, PAD, and CLI.

Turning to FIG. 11, a further embodiment of the disclosed invention, including a method of diagnosing CLI versus PAD via FHS to TNO levels is described. This embodiment of the disclosed invention employs measurement of plasma sulfide and nitric oxide metabolites to clinically determine peripheral artery disease versus critical limb ischemia. Specifically, the ratio of free hydrogen sulfide to total nitric oxide (FHS:TNO) delineates between peripheral artery disease versus critical limb ischemia. The FHS:TNO ratio was found to be lower in CLI patients than PAD patients. In one embodiment, CLI is diagnosed when the FHS:TNO ratio is less than 5, or less than 3, or less than 2. In another embodiment CLI is diagnosed when the FHS:TNO ratio is less than one half, less than one third, less than one fourth, less than one fifth, or less than one sixth of a ratio for PAD patients. This method may also provide a useful therapeutic indicator for clinical interventions that may be followed over time. This method can be used in a diagnostic kit. The embodiment may include treating for CLI or PAD respectively with currently known treatments once the appropriate diagnosis is made.

One product of this embodiment of the disclosed invention would be a method to detect peripheral artery disease or critical limb ischemia beyond the limited clinical diagnosis of ankle brachial index or claudication. A secondary product would be a treatment target to clinically treat disease. Treatment with L-propionyl-carnitine and/or Prostaglandin E1, aspirin, and therapeutics which increase NO levels, including sodium nitrite and therapeutics that increase xanthine oxidase (XO) associated nitrite conversion to nitric oxide and/or increase nitrite conversion to nitric oxide via DADS, for example, may follow diagnosis of CLI.

The technology could be used to accurately diagnose PAD or CLI that is currently imprecise in clinical settings. The approach would also be useful as a point of care device to confirm sulfide and/or nitric oxide levels.

Turning to FIG. 12, a further embodiment of the disclosed invention, including a method of diagnosing CLI versus PAD via THS to TNO levels is described. This embodiment of the disclosed invention employs measurement of plasma sulfide and nitric oxide metabolites to clinically determine peripheral artery disease versus critical limb ischemia. Specifically, the ratio of total hydrogen sulfide to total nitric oxide (THS:TNO) delineates between peripheral artery disease versus critical limb ischemia. The THS:TNO ratio was found to be lower in CLI patients than PAD patients. In one embodiment, CLI is diagnosed when the THS:TNO ratio is less than 10, or less than 5. In another embodiment CLI is diagnosed when the THS:TNO ratio is less than one half, less than one third, less than one fourth, or less than one fifth of a ratio for PAD patients. This method may also provide a useful therapeutic indicator for clinical interventions that may be followed over time. This method can be used in a diagnostic kit. The embodiment may include treating for CLI or PAD respectively with currently known treatments once the appropriate diagnosis is made.

One product of this embodiment of the disclosed invention would be a method to detect peripheral artery disease or critical limb ischemia beyond the limited clinical diagnosis of ankle brachial index or claudication. A secondary product would be a treatment target to clinically treat disease. Treatment with L-propionyl-carnitine and/or Prostaglandin E1, aspirin, and therapeutics which increase NO levels, including sodium nitrite and therapeutics that increase xanthine oxidase (XO) associated nitrite conversion to nitric oxide and/or increase nitrite conversion to nitric oxide via DADS, for example, may follow diagnosis of CLI.

The technology could be used to accurately diagnose PAD or CLI that is currently imprecise in clinical settings. The approach would also be useful as a point of care device to confirm sulfide and/or nitric oxide levels.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, I/we claim:

1. A method of diagnosing and treating critical limb ischemia (CLI) versus non-critical limb ischemic peripheral artery disease (PAD) in a patient comprising:
   determining a patient indicator value, where the patient indicator value is one of;
      a total hydrogen sulfide metabolite plasma level of less than 0.75 µM,
      a total nitric oxide, nitrite, and nitrite (NOx) plasma, level of over 220 nM,
      a ratio of free hydrogen sulfide plasma level to total NOx plasma level is less than 5.0, and
      a ratio of total hydrogen sulfide metabolite plasma level and total NOx plasma level is less than 10;
   diagnosing the patient with as having CLI based on the patient indicator value; and
   administering to the patient a therapeutic for CLI.

2. The method of claim 1 further comprising diagnosing the patient with CLI when the indicator value is total hydrogen sulfide plasma level and the total hydrogen sulfide plasma level is one of less than 0.75 µM, less than 0.70 µM, less than 0.65 µM, less than 0.60 µM, and less than 0.55 µM.

3. The method of claim 1 further comprising diagnosing the patient with CLI when the indicator value is total hydrogen sulfide plasma level and the total hydrogen sulfide plasma level is less than 80% of an average total hydrogen sulfide plasma level for PAD patients.

4. The method of claim 1 further comprising diagnosing the patient with CLI when the indicator value is total NOx plasma level and the total NOx plasma level is one of over 220 nM, over 200 nM, over 175 nM, and over 150 nM.

5. The method of claim 1 further comprising diagnosing the patient with CLI when the indicator value is total NOx plasma level and the total NOx plasma level is one of more two times, more than three times, and more than fourth times of an average total NOx plasma level for PAD patients.

6. The method of claim 1 further comprising diagnosing the patient with CLI when
   the indicator value is the ratio of free hydrogen sulfide plasma level to total NOx plasma level and
   the ratio of free hydrogen sulfide plasma level to total NOx plasma level is one of less than 5.0, or less than 3.0, and less than 2.0.

7. The method of claim 1 further comprising diagnosing the patient with CLI when
   the indicator value is the ratio of free hydrogen sulfide plasma level to total NOx plasma level and
   the ratio of free hydrogen sulfide plasma level to total NOx plasma level is one of less than one half, less than one third, less than one fourth, less than one fifth, and less than one sixth of an average ratio of free hydrogen sulfide plasma level to total NOx plasma level for PAD patients.

8. The method of claim 1 further comprising diagnosing the patient with CLI when
   the indicator value is the ratio of total hydrogen sulfide metabolite plasma level and total NOx plasma level and
   the ratio of total hydrogen sulfide metabolite plasma level and total NOx plasma level is one of less than 10 and less than 5.

9. The method of claim 1 further comprising diagnosing the patient with CLI when
   the indicator value is the ratio of total hydrogen sulfide metabolite plasma level and total NOx plasma level and
   the ratio of total hydrogen sulfide metabolite plasma level and total NOx plasma level is one of less than one half, less than one third, less than one fourth, and less than one fifth of an average ratio of total hydrogen sulfide metabolite plasma level and total NOx plasma level for PAD patients.

10. The method of claim 6 further comprising diagnosing the patient with CLI only if the ratio of free hydrogen sulfide plasma level to total NOx plasma level is also one of less than one half, less than one third, less than one fourth, less than one fifth, and less than one sixth of an average ratio of free hydrogen sulfide plasma level to total NOx plasma level for PAD patients.

11. The method of claim 6 wherein the indicator value further includes the ratio of total hydrogen sulfide metabolite plasma level and total NOx plasma level and
   further comprising diagnosing the patient with CLI only when the ratio of total hydrogen sulfide metabolite plasma level and total NOx plasma level is also one of less than 10 and less than 5.

12. The method of claim 6 wherein the indicator value further includes the ratio of total hydrogen sulfide metabolite plasma level and total NOx plasma level and
   further comprising diagnosing the patient with CLI only when a total hydrogen sulfide metabolite plasma level and total NOx plasma level is one of less than one half, less than one third, less than one fourth, and less than one fifth of an average ratio of total hydrogen sulfide metabolite plasma level and total NOx plasma level for PAD patients.

13. The method of claim 1 wherein the therapeutic one of increases xanthine oxidase (XO) associated nitrite conversion to nitric oxide and increases nitrite conversion to nitric oxide via diallyl disulfide (DADS).

14. The method of claim 13 wherein the therapeutic increases XO associated nitrite conversion to nitric oxide and the therapeutic includes diallyl trisulfide (DATS) or a pharmacologically acceptable salt, solvate, ester, amide, clathrate, stereoisomer, enantiomer, prodrug or analog thereof, or combination thereof.

15. The method of claim 14 wherein the therapeutic further includes one of XO, nitrite, both XO and nitrite, and pharmacologically acceptable salts, solvates, esters, amides, clathrates, stereoisomers, enantiomers, prodrugs or analogs thereof, or combinations thereof.

16. The method of claim 13 wherein the therapeutic increases nitrite conversion to nitric oxide via DADS and the therapeutic includes DADS or a pharmacologically acceptable salt, solvate, ester, amide, clathrate, stereoisomer, enantiomer, prodrug or analog thereof, or combination thereof.

17. The method of claim 16 wherein the therapeutic further includes one of nitrite and a pharmacologically acceptable salt, solvate, ester, amide, clathrate, stereoisomer, enantiomer, prodrug or analog thereof, or combination thereof.

* * * * *